United States Patent
Riondel et al.

(10) Patent No.: US 7,084,296 B2
(45) Date of Patent: Aug. 1, 2006

(54) METHOD FOR MAKING AQUEOUS SOLUTIONS OF (METH)ACRYLOYLOXY-ETHYLBENZYLDIMETHYLAMMONIUM CHLORIDES

(75) Inventors: Alain Riondel, Forbach (FR); Gilles Herbst, Nancy (FR); Serge Tretjak, Rouhling (FR)

(73) Assignee: Arkema, Paris LaDefence Cedex (FR)

( * ) Notice: Subject to any disclaimer, the term of this patent is extended or adjusted under 35 U.S.C. 154(b) by 358 days.

(21) Appl. No.: 10/344,322

(22) PCT Filed: Aug. 7, 2001

(86) PCT No.: PCT/FR01/02563

§ 371 (c)(1),
(2), (4) Date: Aug. 4, 2003

(87) PCT Pub. No.: WO02/14258

PCT Pub. Date: Feb. 21, 2002

(65) Prior Publication Data

US 2004/0024242 A1    Feb. 5, 2004

(30) Foreign Application Priority Data

Aug. 11, 2000  (FR) .................. 00 10568

(51) Int. Cl.
*C07C 69/52* (2006.01)
(52) U.S. Cl. ...................................... 560/222
(58) Field of Classification Search .................. None
See application file for complete search history.

(56) References Cited

FOREIGN PATENT DOCUMENTS

| FR | 2788767 | 7/2000 |
|----|---------|--------|
| WO | WO 0043348 | 7/2000 |

*Primary Examiner*—Paul A. Zucker
(74) *Attorney, Agent, or Firm*—Millen, White, Zelano & Branigan, P.C.

(57) ABSTRACT

This process for the manufacture of an aqueous solution of (meth)acryloyloxyethylbenzyl-dimethylammonium chloride ((M)ADAMQUAT BZ) by reaction, in the presence of water, of N,N-dimethylaminoethyl (meth)acrylate ((M)ADAME) with benzyl chloride is characterized in that the reaction is carried out continuously in a reactor operating according to the perfectly stirred reactor technology.

20 Claims, No Drawings

METHOD FOR MAKING AQUEOUS SOLUTIONS OF (METH)ACRYLOYLOXY-ETHYLBENZYLDIMETHYLAMMONIUM CHLORIDES

The present invention relates to a process for the manufacture of aqueous solutions of acryloyloxyethylbenzyldimethylammonium chloride (ADAMQUAT BZ) and methacryloyloxyethylbenzyl-dimethylammonium chloride (MADAMQUAT BZ) quaternary salts by reaction, in the presence of water, of N,N-dimethylaminoethyl acrylate (ADAME) and N,N-dimethylaminoethyl methacrylate (MADAME) respectively with benzyl chloride as quaternizing agent.

Aqueous solutions of these quaternary salts (which generally assay 80% by weight of active materials) are used to prepare polymers intended to act as cationic flocculants in water treatment.

European Patent EP-B-250 325 discloses a process for the preparation of aqueous solutions of quaternary salts, including ADAMQUAT BZ and MADAMQUAT BZ, according to which process, in the presence of at least one polymerization inhibitor:

in a first stage (a), the (M)ADAME is reacted with 5 to 20% by weight of the amount by weight of the quaternizing agent necessary for the reaction or, according to an alternative form (a'), with 5 to 20% by weight, with respect to the weight of the (M)ADAME, of an aqueous solution of quaternary salts, which solution comprises from 50 to 85% by weight of quaternary salts; and in a second stage (b), water and the quaternizing agent are added continuously until the desired concentration of quaternary salts in the water is obtained.

During stages (a) and (b), the temperature is maintained at a value of between 30 and 60° C. Furthermore, during stages (a) and (b) and in particular near the end of the reaction, a stream of oxygenated gas is maintained in the reaction medium such that the ratio by volume (or volumetric throughput) of total gas at the outlet of the reactor to the volume (or volumetric throughput) of oxygen introduced at the inlet of this same reactor is less than 100.

This process makes it possible to prepare aqueous solutions of quaternary salts which have a stability at ambient temperature of greater than one year. However, a particularly high content of impurities, in particular of

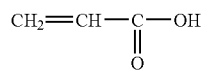

and of

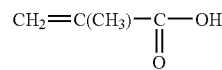

respectively, is found in these solutions.

In addition, this process requires relatively long reaction times, which represents an obvious economic disadvantage.

A process intended to reduce the formation of the impurities during the quaternization reaction was then provided in international application WO 89/07588. In accordance with this process, the reaction is carried out at a temperature of between 10 and 80° C., and in a first stage, all or a portion of the quaternizing agent necessary for the reaction is introduced into the reactor, this agent being in the liquid state under the reaction conditions, subsequently, (M)ADAME is added, and as soon as 0 to 30% of the stoichiometry of the (M)ADAME has been introduced into the reactor, the remainder of the quaternizing agent, the remainder of the (M)ADAME and the water are continuously and simultaneously added until the desired concentration of quaternary salts is obtained, and, in the case where the quaternizing agent is introduced in the gaseous state at the reaction temperature, the reaction is carried out in the presence of oxygen and a pressure is applied so that the quaternizing agent is liquid at the reaction temperature and, at the end of the reaction, the pressure is gradually decreased to atmospheric pressure and, simultaneously, a ratio of volumetric throughput of total gas at the outlet of the reactor to the volumetric throughput of oxygen introduced into the reactor of less than 100 is imposed.

The above process according to WO 89/07588 introduces significant improvements to the process according to EP-B-250 325. However, it transpired that the purity with which the quaternary salts are obtained is still insufficient. Thus, this process makes it possible to significantly reduce the content of (meth)acrylic acid resulting from the hydrolysis of the (M)ADAME. On the other hand, it results in a (M)ADAMQUAT BZ comprising a significant amount of benzyl alcohol (500 to 2600 ppm), which impurity results from the hydrolysis of benzyl chloride and renders the (M)ADAMQUAT BZ unsuitable for use thereof in polymerization.

The Assignee Company has thus looked for operating conditions for the preparation of aqueous solutions of ADAMQUAT BZ and of MADAMQUAT BZ which are capable of minimizing the abovementioned impurities, so as to provide these salts in aqueous solution of very high analytical quality, while reducing the duration of the reaction.

This novel process, which thus forms the subject-matter of the present invention, is characterized in that the reaction is carried out continuously in a reactor operating according to the perfectly stirred reactor technology (cf. Techniques de l'Ingénieur, Volume J3 Génie des procédés—Réacteurs—Procédés Industriels [Techniques of the Engineer, Volume J3, Process Engineering—Reactors—Industrial Processes]).

In comparison with known batch processes, the process of the invention makes it possible to improve the productive output and to reduce the reaction volume, and thus to improve safety, while offering the advantage of providing a product of uniform quality.

Furthermore, the reaction according to the invention is generally carried out with a molar ratio of the (M)ADAME to the benzyl chloride which is between 1 and 1.1, in particular between 1.02 and 1.05. With regard to the ratio of the benzyl chloride/water introduction throughputs, it is generally between 1.8 and 2.5, in particular between 2 and 2.2.

The reaction according to the invention is generally carried out with a residence time of 1 to 8 hours, in particular between 2 and 6 hours. The temperature is generally between 25 and 55° C., in particular between 35 and 50° C. The process of the invention is furthermore generally carried out at atmospheric pressure.

In accordance with a particularly preferred embodiment, the reactor is initially filled with a 75–80% by weight aqueous solution of (meth)acryloyloxyethylbenzyldimethylammonium chloride and, subsequently, the water, the (M)ADAME and the benzyl chloride are introduced simultaneously.

The process according to the present invention is furthermore advantageously carried out in the presence of at least one stabilizer chosen in particular from 3,5-di(tert-butyl)-4-hydroxytoluene, hydroquinone methyl ether, hydroquinone, catechol, tert-butylcatechol and the mixtures of these stabilizers, the content of stabilizing agent(s) being in particular from 20 to 2 000 ppm, preferably from 100 to 1 200 ppm, with respect to the aqueous solution of (meth)acryloyloxyethylbenzyldimethylammonium chloride.

In addition, the process according to the invention is advantageously carried out in the presence of at least one sequestering agent for metals chosen in particular from diethylenetriaminepentaacetic acid, the pentasodium salt of diethylenetriaminepentaacetic acid, N-(hydroxyethyl)ethylenediaminetriacetic acid and the trisodium salt of N-(hydroxyethyl)ethylenediaminetriacetic acid, the content of sequestering agent(s) being in particular from 1 to 100 ppm, preferably from 5 to 30 ppm, with respect to the aqueous solution of (meth)acryloyloxyethylbenzyldimethylammonium chloride.

Generally, the sequestering agents are added in the form of an aqueous solution, as they are generally available in this form. Thus, the pentasodium salt of diethylenetriaminepentaacetic acid sold under the name Versenex 80 is provided in the form of an approximately 40% by weight aqueous solution.

The process according to the invention makes it possible in particular to prepare aqueous solutions which have a concentration of (M)ADAMQUAT BZ of 50 to 85% by weight and which comprise very low amounts of impurities, as illustrated in the table below.

The following example illustrates the present invention without, however, limiting the scope thereof.

EXAMPLE

Preparation of ADAMQUAT BZ 700 g of ADAMQUAT BZ 80 are charged to a reactor with a capacity of one litre operating according to the perfectly stirred reactor technology and are brought to 38° C. with stirring and while bubbling in air. Subsequently, the ADAME (stabilized with 800 ppm of HQME), the water and the benzyl chloride are introduced simultaneously at targeted respective throughputs of 75.7 g/h (0.529 mol/h), 31.5 g/h and 65.65 g/h (0.518 mol/h) respectively, i.e. an ADAME/benzyl chloride molar ratio of 1.02 and a benzyl chloride/water ratio by weight of 2.084.

The withdrawal throughput of the finished product by overflowing is 171.7 g/h, i.e. an overall residence time of 4 hours.

After an operating time arbitrarily set at 6 h, i.e. 1.5 residence time, the product is analysed by HPLC. It exhibits the following characteristics:

| HPLC analysis | Content (ppm) |
|---|---|
| Acrylic acid | 3 418 |
| Benzyl chloride | <10 |
| Benzyl alcohol | 72 |

The invention claimed is:

1. A process for the manufacture of an aqueous solution of (meth)acryloyloxyethylbenzyldimethyl-ammonium chloride ((M)ADAMQUAT BZ) by reaction, in the presence of water, of N,N-dimethylaminoethyl (meth)acrylate ((M)ADAME) with benzyl chloride, wherein the reaction is carried out continuously in a reactor operating according to the Perfectly Stirred Reactor Technology, and wherein the reaction is carried out with a ratio of the benzyl chloride/water introduction throughputs of between 1.8 and 2.5.

2. A process according to claim 1, wherein the reaction is carried out with a molar ratio of the (M)ADAME to the benzyl chloride which is between 1 and 1.1.

3. A process according to claim 1, wherein the reaction is carried out with a residence time of 1 to 8 hours.

4. A process according to claim 1, wherein the reaction is carried out at a temperature of 25 to 55° C.

5. A process according to claim 1, wherein the reaction is carried out at atmospheric pressure.

6. A process according to claim 1, wherein the reactor is initially filled with a 75–80% by weight aqueous solution of (meth)acryloyloxyethylbenzyldimethylammonium chloride and, subsequently, the water, the (M)ADAME and the benzyl chloride are introduced simultaneously.

7. A process according to claim 1, which is carried out in the presence of at least one stabilizer selected from the group consisting of 3,5-di(tert-butyl)-4-hydroxytoluene, hydroquinone methyl ether, hydroquinone, catechol, tert-butylcatechol and the mixtures of these stabilizers, wherein the content of stabilizing agent(s) is from 20 to 2 000 ppm, with respect to the aqueous solution of (meth)acryloyloxyethylbenzyldimethylammonium chloride.

8. A process according to claim 1, which is carried out in the presence of at least one sequestering agent for metals selected from the group consisting of diethylenetriaminepentaacetic acid, the pentasodium salt of diethylene-triaminepentaacetic acid, N-(hydroxyethyl)ethylene-diaminetriacetic acid and the trisodium salt of N-(hydroxyethyl)ethylene-diaminetriacetic acid, wherein the content of sequestering agent(s) is from 1 to 100 ppm, with respect to the aqueous solution of (meth)acryloyloxy-ethylbenzyldimethylammonium chloride.

9. A process according to claim 1 wherein the reaction is conducted with a ratio of the benzylchloride/water introduction throughputs of between 2 and 2.2.

10. A process according to claim 1 wherein the molar ratio of the (M)ADAME to the benzylchoride is between 1.02 and 1.05.

11. A process according to claim 10 wherein the reaction is conducted at a temperature of 35–50° C.

12. A process for the manufacture of an aqueous solution of (meth)acryloyloxyethylbenzyldimethyl-ammonium chloride ((M)ADAMQUAT BZ) by reaction, in the presence of water, of N,N-dimethylaminoethyl (meth)acrylate ((M)ADAME) with benzyl chloride, wherein the reaction is carried out continuously in a reactor operating according to the Perfectly Stirred Reactor Technology and wherein the reaction is conducted at atmospheric pressure.

13. A process according to claim 12, wherein the reaction is carried out with a molar ratio of the (M)ADAME to the benzyl chloride which is between 1 and 1.1.

14. A process according to claim 13, wherein the reaction is carried out with a residence time of 1 to 8 hours.

15. A process according to claim 12, wherein the reaction is carried out at a temperature of 25 to 55° C.

16. A process according to claim 12, wherein the reactor is initially filled with a 75–80% by weight aqueous solution of (meth)acryloyloxyethylbenzyldimethylammonium chloride and, subsequently, the water, the (M)ADAME and the benzyl chloride are introduced simultaneously.

17. A process according to claim 12, which is carried out in the presence of at least one stabilizer selected from the group consisting of 3,5-di(tert-butyl)-4-hydroxytoluene, hydroquinone methyl ether, hydroquinone, catechol, tert-butylcatechol and the mixtures of these stabilizers, wherein the content of stabilizing agent(s) is from 20 to 2 000 ppm, with respect to the aqueous solution of (meth)acryloyloxy-ethylbenzyldimethylammonium chloride.

18. A process according to claim 12, which is carried out in the presence of at least one sequestering agent for metals selected from the group consisting of diethylenetriaminepentaacetic acid, the pentasodium salt of diethylene-tri-aminepentaacetic acid, N-(hydroxyethyl)ethylene-diaminetriacetic acid and the trisodium salt of N-(hydroxyethyl)ethylenediaminetriacetic acid, wherein the content of sequestering agent(s) is from 1 to 100 ppm, with respect to the aqueous solution of (meth)acryloyloxy-ethylbenzyldimethylammonium chloride.

19. A process according to claim 12 wherein the reaction is conducted with a ratio of the benzylchloride/water introduction throughputs of between 2 and 2.2.

20. A process according to claim 12 wherein the molar ratio of the (M)ADAME to the benzylchoride is between 1.02 and 1.05, and wherein the temperature is 35–50° C.

* * * * *

UNITED STATES PATENT AND TRADEMARK OFFICE
CERTIFICATE OF CORRECTION

| | |
|---|---|
| PATENT NO. | : 7,084,296 B2 |
| APPLICATION NO. | : 10/344322 |
| DATED | : August 1, 2006 |
| INVENTOR(S) | : Alain Riondel |

It is certified that error appears in the above-identified patent and that said Letters Patent is hereby corrected as shown below:

On the Title page, #73 Assignee: reads "LaDefence" should read -- La Defense --
Column 5, line 4, reads "according to claim 13," should read -- according to claim 12, --

Signed and Sealed this

Sixth Day of March, 2007

JON W. DUDAS
*Director of the United States Patent and Trademark Office*